(12) United States Patent
Mustacich

(10) Patent No.: US 10,302,605 B2
(45) Date of Patent: May 28, 2019

(54) COLUMN ASSEMBLY FOR A GAS CHROMATOGRAPH

(75) Inventor: Robert V. Mustacich, Santa Barbara, CA (US)

(73) Assignee: AGILENT TECHNOLOGIES, INC., Loveland, CO (US)

( * ) Notice: Subject to any disclaimer, the term of this patent is extended or adjusted under 35 U.S.C. 154(b) by 987 days.

(21) Appl. No.: 13/364,719

(22) Filed: Feb. 2, 2012

(65) Prior Publication Data

US 2012/0198913 A1 Aug. 9, 2012

Related U.S. Application Data

(60) Provisional application No. 61/440,352, filed on Feb. 7, 2011.

(51) Int. Cl.
| | | |
|---|---|---|
| *G01N 30/02* | (2006.01) | |
| *G01N 30/60* | (2006.01) | |
| *G01N 30/54* | (2006.01) | |
| *G01N 30/30* | (2006.01) | |

(52) U.S. Cl.
CPC ............. *G01N 30/60* (2013.01); *G01N 30/30* (2013.01); *G01N 30/54* (2013.01); *Y10T 29/4935* (2015.01)

(58) Field of Classification Search
CPC ................................ B01D 15/08; G01N 30/02
USPC ............ 73/23.35, 23.39–23.42, 592, 890.03; 95/17, 82, 87, 102, 105; 96/101; 29/592, 29/890.03; 165/172, 176, 184, 186, 910
See application file for complete search history.

(56) References Cited

U.S. PATENT DOCUMENTS

| | | | |
|---|---|---|---|
| 4,043,905 A | | 8/1977 | Novotny et al. |
| 4,207,188 A | | 6/1980 | Tsuda et al. |
| 4,805,441 A | * | 2/1989 | Sides ............... G01N 30/00 422/89 |
| 5,152,176 A | * | 10/1992 | Bryselbout et al. ......... 73/23.41 |
| 5,552,042 A | * | 9/1996 | Le Febre et al. .......... 210/198.2 |
| 5,599,455 A | | 2/1997 | Hukai |
| 6,209,386 B1 | * | 4/2001 | Mustacich et al. .......... 73/23.39 |
| 6,217,829 B1 | | 4/2001 | Mustacich et al. |
| 6,333,088 B1 | * | 12/2001 | Le Febre et al. .......... 428/36.91 |
| 6,354,136 B1 | * | 3/2002 | Bremer ................ G01N 30/30 210/198.2 |
| 6,490,852 B1 | * | 12/2002 | Mustacich et al. .................. 57/3 |
| 6,530,260 B1 | | 3/2003 | Mustacich et al. |
| 6,579,345 B2 | * | 6/2003 | Munari et al. .................... 95/87 |

(Continued)

FOREIGN PATENT DOCUMENTS

| | | |
|---|---|---|
| EP | 0488942 A3 | 12/1992 |
| EP | 1837650 A1 | 9/2007 |
| GB | 2423266 | 8/2006 |

OTHER PUBLICATIONS

Office Action dated Sep. 29, 2014 in Chinese Application No. 201210028705.5.

*Primary Examiner* — Daniel S Larkin

(57) ABSTRACT

A column assembly for gas chromatography, which is coolable by a fluid, includes a capillary column, a heating element for heating at least a portion of the capillary column, and a tube having a lumen and in contact with at least one of the capillary column and the heating element. When energized, the heating element raises the temperature of the capillary column. To lower the temperature of the capillary column, a fluid flows through the tube, and heat is transferred from the capillary column to the fluid in the tube.

20 Claims, 6 Drawing Sheets

(56) References Cited

U.S. PATENT DOCUMENTS

| | | |
|---|---|---|
| 6,666,074 B2 | 12/2003 | Gerner et al. |
| 6,682,699 B2 | 1/2004 | Mustacich et al. |
| 6,751,983 B1 * | 6/2004 | Dienhart ............... B60H 1/3227 165/155 |
| 7,228,067 B2 * | 6/2007 | Magni et al. ................. 392/480 |
| 7,303,610 B2 * | 12/2007 | Zilioli et al. .................... 96/101 |
| 7,409,850 B2 * | 8/2008 | Traudt ......................... 73/23.35 |
| 7,661,460 B1 * | 2/2010 | Cowans ................. F28D 7/024 165/140 |
| 7,914,612 B2 * | 3/2011 | Rubey et al. .................... 96/101 |
| 7,984,638 B2 * | 7/2011 | White .......................... 73/23.41 |
| 8,117,895 B2 * | 2/2012 | Currie et al. ............... 73/23.35 |
| 2003/0037592 A1 | 2/2003 | D'Couto et al. |
| 2004/0159110 A1 * | 8/2004 | Janssen .................... F24D 3/18 62/77 |
| 2006/0124285 A1 * | 6/2006 | Kite ....................... F28D 7/024 165/163 |
| 2009/0173146 A1 * | 7/2009 | Pursch et al. ................. 73/61.52 |
| 2010/0000943 A1 | 1/2010 | Carson et al. |

\* cited by examiner

COLUMN ASSEMBLY FOR A GAS CHROMATOGRAPH

CROSS REFERENCE TO RELATED APPLICATION

This claims the benefit of U.S. Provisional Patent Application No. 61/440,352, filed on Feb. 7, 2011, the disclosure of which is incorporated by reference in its entirety.

BACKGROUND

Gas chromatography is commonly practiced at temperatures above ambient temperature with the separation column temperature usually controlled by installing it in a convection oven. The oven thermal control systems usually rely on ambient for downward temperature adjustment of the column assembly of a gas chromatography instrument. The maximum rate of this downward temperature adjustment is typically achieved by turning off any heating and applying forced air convection where possible. Because the rate of heat exchange is proportional to the temperature difference, this rate of cooling slows as the oven approaches ambient temperature. The more massive and more insulated the oven is, the slower this process can be. To cool more quickly than the physical limits imposed by convection and conduction for a specific design, or to cool to temperatures below the ambient limit, a different means to remove heat must be used, such as cryogenic liquids or a thermoelectric cooler.

Cryogenic liquids are liquids having low boiling temperatures at ambient pressure. Cryogenic liquids can be delivered mechanically and released at the point of the desired cooling. The rapid vaporization and expansion of the resulting gas results in a large drop in temperature from evaporative cooling and Joule-Thomson cooling. Most commonly, cylinders of liquid carbon dioxide are valved and discharged into the entire interior oven of a gas chromatography instrument to provide Joule-Thomson cooling. This is an inefficient and expensive process, because entire cylinders can be discharged quickly to cool the ovens of the gas chromatography instrument repeatedly. In thermoelectric cooling (or Peltier cooling), a solid-state active heat pump transfers heat from one side of the device to the other. Thermoelectric cooling, however, is practically limited to smaller sizes of gas chromatography instruments and provides limited rates of heat transfer. Thermoelectric cooling also requires large electrical currents with significant heat dissipation for its heat pumping process. Because cryogenic liquids can cool effectively, as compared to thermoelectric cooling, discharge of a cryogenic liquid into the oven of a gas chromatography instrument is the conventional method for cooling a gas chromatography (GC) column.

The development of low thermal mass (LTM) gas chromatography column assemblies eliminated the effective mass of the conventional gas chromatography oven as an obstacle to rapid heating and cooling of the gas chromatography column. However, the cooling rate of such a conventional LTM column assembly is still dependent upon the convection conditions, the difference between the column temperature and ambient temperature, and the low thermal mass device surface area. While cooling faster than ordinary gas chromatography ovens because of the smaller mass, the time spent cooling the column is still unproductive waiting time and should be minimized in order to maximize the productive utilization of a gas chromatography instrument. Also, low thermal mass gas chromatography instruments are unable to lower the column temperature below the ambient temperature.

Thus, what is needed are devices and methods for quickly cooling the column of a gas chromatography instrument and maintaining subambient temperatures, without the wasteful and expensive use of relatively large amounts of cryogenic liquids.

BRIEF DESCRIPTION OF THE DRAWINGS

The accompanying drawings, which are incorporated in and constitute a part of this specification, illustrate several embodiments of the invention and together with the description, serve to explain the principles of the invention.

DETAILED DESCRIPTION

Figure 1:
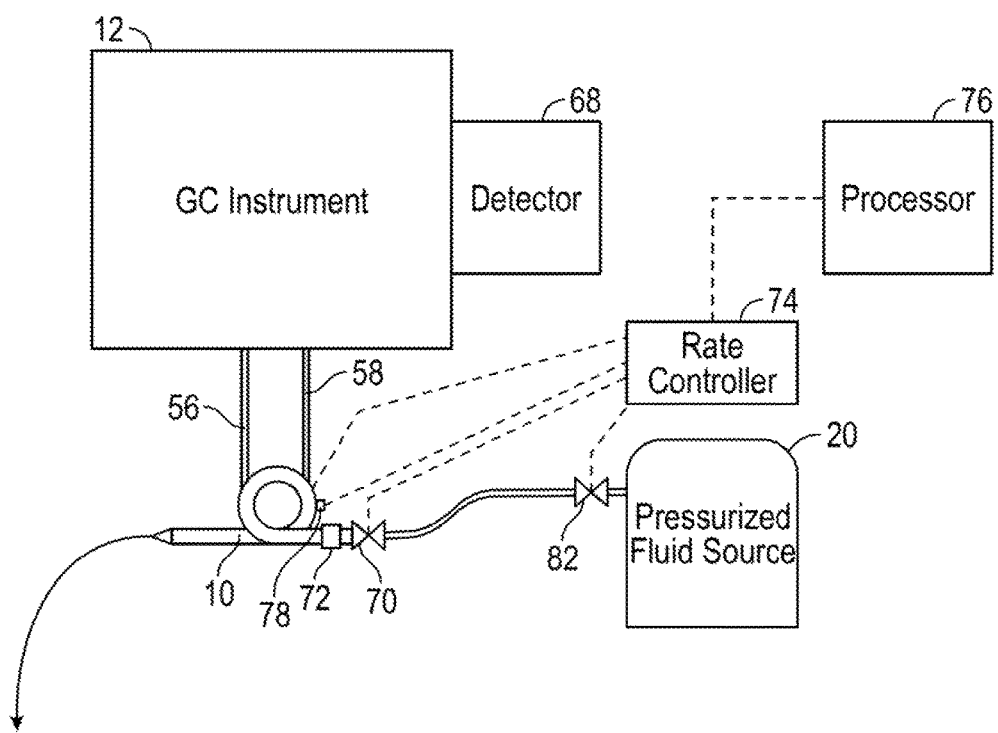
FIG. 1 is a schematic view of a gas chromatography instrument, according to one aspect.

The present invention may be understood more readily by reference to the following detailed description, examples, drawings, and claims, and their previous and following description. However, before the present devices, systems, and/or methods are disclosed and described, it is to be understood that this invention is not limited to the specific devices, systems, and/or methods disclosed unless otherwise specified, as such can, of course, vary. It is also to be understood that the terminology used herein is for the purpose of describing particular aspects only and is not intended to be limiting.

As used in the specification and the appended claims, the singular forms "a," "an" and "the" include plural referents unless the context clearly dictates otherwise. Thus, for example, reference to a "column" can include two or more such columns unless the context indicates otherwise.

Ranges may be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

As used herein, the terms "optional" or "optionally" mean that the subsequently described event or circumstance may or may not occur, and that the description includes instances where said event or circumstance occurs and instances where it does not.

Disclosed are column assemblies comprising a capillary column having a front end and a rear end, a heating element for heating at least a portion of the capillary column, and a tube having an exterior surface and defining a lumen, the tube configured for receiving a cooling fluid to pass through the lumen, wherein the tube is positioned relative to the capillary column and the heating element such that as cooling fluid is passed through the tube, the temperature of both the capillary column and the heating element is reduced.

Also disclosed are column assemblies that further comprise a temperature sensor configured to measure the temperature of the capillary column.

Also disclosed are column assemblies, wherein the heating element comprises an elongate wire, and wherein the capillary column and the elongate wire are helically wound around the tube.

Also disclosed are column assemblies, wherein both the capillary column and the elongate wire are in contact with the exterior surface of the tube.

Also disclosed are column assemblies, wherein the heating element wraps around the tube, and the capillary column wraps around the combination of the heating element and the tube.

Also disclosed are column assemblies, wherein the capillary column wraps around the tube, and the heating element wraps around the combination of the capillary column and the tube.

Also disclosed are column assemblies, wherein a portion of the tube forms a loop, wherein the heating element comprises an elongate wire helically wound around said portion of the tube, and at least a portion of the capillary column wraps around the combination of the elongate wire and the portion of the tube.

Also disclosed are column assemblies that further comprise one or more electrically insulating layers positioned between electrically conductive components such as the elongate wire, the tube, and outer foil covering. A thin layer of a non-electrically conducting material can provide electrical insulation and sufficient thermal conduction for rapid heat transfer between the elongate wire, tube, and outer foil covering.

Also disclosed are column assemblies, wherein the heating element comprises the tube.

Also disclosed are column assemblies, wherein the capillary column is helically wound around the tube.

Also disclosed are column assemblies that further comprise a throttling device in fluid communication with the lumen of the tube.

Also disclosed are column assemblies, wherein the throttling device comprises a valve.

Also disclosed are gas chromatography instruments, comprising a column assembly as disclosed above, a sample inlet for introducing a sample into the front end of the capillary column, a carrier gas inlet for introducing a carrier gas into the front end of the capillary column, and a detector in fluid communication with the rear end of the capillary column.

Also disclosed are methods that comprise the steps of: providing a column assembly as disclosed above, and adjusting the temperature of the capillary column by controlling the heating element as well as a flow of the cooling fluid through the tube.

Also disclosed are methods, wherein adjusting the temperature of the capillary column comprises heating with the heating element, turning off the heating element when it is desired to cool the capillary column, and turning on said flow of cooling fluid.

Also disclosed are methods, wherein adjusting the temperature of the capillary column comprises heating with the heating element for a predetermined duration of time, turning off the heating element, and turning on said flow of cooling fluid.

Also disclosed are methods, wherein adjusting the temperature of the capillary column comprises simultaneously heating with said heating element and cooling with said flow of cooling fluid.

Also disclosed are methods, wherein adjusting the temperature of the capillary column comprises heating with the heating element, turning on said flow of cooling fluid when the capillary column reaches a predetermined temperature, and controlling said heating and said flow to maintain the temperature of the capillary column in a predetermined range.

Also disclosed are methods, wherein the heating element comprises the tube, the capillary column is helically wound around the tube, and said adjusting comprises heating the tube to result in heating of the capillary column.

Also disclosed are methods, wherein adjusting the temperature of the capillary column is performed to result in a temperature change rate of about $-100°$ C. per second to about $20°$ C. per second.

Also disclosed are methods for gas chromatography (GC), comprising heating a capillary column to cause a temperature increase of an analyte in the capillary column with a heating element adjacent to the capillary column, and passing a cooling fluid through a tube that is adjacent to both the capillary column and the heating element to maintain or lower the temperature of the capillary column and the heating element.

Also disclosed are column assemblies for gas chromatography, the column assemblies coolable by a fluid and comprising a tube having an exterior surface surrounding and defining a lumen, wherein the lumen is configured for receiving the fluid therein, a heating element positioned in contact with at least a portion of the exterior surface of the tube, wherein the heating element has a first surface directed towards the tube and a second surface directed away from the tube, and a capillary column, wherein at least a portion of the capillary column is positioned in contact with at least a portion of the second surface of the heating element.

Also disclosed are column assemblies for gas chromatography that further comprise a throttling device positioned in fluid communication with the lumen of the tube. In one aspect, the throttling device comprises an orifice, and in another aspect, the throttling device comprises a valve or a frit.

Also disclosed are column assemblies for gas chromatography, wherein the tube of the column assemblies is formed from a material having a high thermal conductivity. In one aspect, the tube is formed of aluminum.

Also disclosed are column assemblies for gas chromatography, wherein at least a portion of the tube of the column assemblies is formed into an arcuate shape. In one aspect, at least a portion of the tube is formed into a loop shape. It is contemplated that the loop shape has an inner diameter of between about 1 inch and about 12 inches. It is also contemplated that the loop shape has an inner diameter of between about 2 inch and about 5 inches. In one example, the loop shape has an inner diameter of about 2.5 inches.

Also disclosed are column assemblies for gas chromatography, wherein at least a portion of the tube of the column assemblies is formed into an arcuate shape, wherein the tube has a first end and a second end, and wherein the first end and the second end of the tube are substantially parallel. In one aspect, at least a portion of the first end of the tube overlies the second end of the tube.

Also disclosed are column assemblies for gas chromatography, wherein the heating element of the column assemblies is an elongated electrical resistive heating wire. In one aspect, the heating wire is helically wound around at least a portion of the exterior surface of the tube. In another aspect, the capillary column of the column assemblies has a predetermined length and is helically wound around at least a portion of the second surface of the heating element. In a further aspect, a pitch of the heating wire is greater than a pitch of the capillary column.

Also disclosed are column assemblies for gas chromatography, wherein the capillary column of the column assemblies has a predetermined length and is helically wound around at least a portion of the second surface of the heating element of the column assemblies. It is contemplated that the capillary column has a length between about 1 meter and about 20 meters. It is also contemplated that the capillary column has a length between about 5 meters and about 15 meters. In an example, the length of the capillary column is about 5 meters. In one aspect, the capillary column is helically wound such that a peripheral surface of a first winding of the capillary column is adjacent to the peripheral surface of a second winding of the capillary column.

Also disclosed are column assemblies for gas chromatography, wherein at least a portion of the column assembly is surrounded by a sheath. In one aspect, the sheath is a layer of metallic foil which can conduct heat over at least a portion of the column assembly.

Also disclosed are column assemblies for gas chromatography, the column assemblies coolable by a fluid and comprising a tube having an exterior surface surrounding and defining a lumen, wherein the lumen is configured for receiving the fluid therein, a capillary column, wherein at least a portion of the capillary column is positioned in contact with at least a portion of the exterior surface of the tube, and means for heating the tube. In one aspect, the means for heating the tube comprises resistively heating the tube.

Also disclosed are methods for controlling a rate of change of temperature of a capillary column of gas chromatography comprising a tube having an exterior surface surrounding and defining a lumen, a heating element positioned in contact with at least a portion of the exterior surface of the tube, wherein the heating element has a first surface directed towards the tube and a second surface directed away from the tube, wherein at least a portion of the capillary column is positioned in contact with at least a portion of the second surface of the heating element. In one aspect, the method comprises flowing a fluid through the lumen of the tube and transferring heat through the heating element and between the capillary column and the fluid in the lumen of the tube.

Also disclosed are methods for controlling a rate of change of temperature of a capillary column of a gas chromatography instrument, wherein the temperature of the capillary column of the gas chromatography instrument is changed at a rate of between about $-200°$ C. and $50°$ C. per second. It is contemplated that that the temperature of the capillary column can be changed at a rate of between about $-150°$ C. and $30°$ C., between about $-120°$ C. and $30°$ C., or between about $-100°$ C. and $30°$ C. per second. In an example, the temperature of the capillary column is changed at a rate of about $-82°$ C. per second.

Also disclosed are gas chromatography instruments for analyzing at least one constituent compound of a sample. A gas chromatography instrument comprises a capillary column assembly comprising a tube having an exterior surface and defining a lumen, a heating element positioned in contact with at least a portion of the exterior surface of the tube, wherein the heating element has a first surface directed towards the tube and a second surface directed away from the tube, and a capillary column, wherein at least a portion of the capillary column is positioned in contact with at least a portion of the second surface of the heating element, a throttling device positioned in fluid communication with the lumen of the tube. The gas chromatography instrument may be connected to a source of pressurized fluid in communication with the lumen of the tube, wherein the pressurized fluid can be selectively discharged through the throttling device and into the lumen of the tube. A gas chromatography instrument may further comprises a detector for analyzing the at least one constituent compound, and a rate controller comprising a valve in fluid communication with the source of pressurized fluid, wherein the rate controller is configured for controlling a rate of change of temperature of the capillary column.

Also disclosed are gas chromatography instruments for analyzing at least one constituent compound of a sample, wherein the pressurized fluid connected to the gas chromatography instrument is a cryogenic liquid. In one aspect, the fluid is carbon dioxide. In a further aspect, the fluid is liquid nitrogen.

Also disclosed are gas chromatography instruments for analyzing at least one constituent compound of a sample, wherein the conduit of the capillary column of a gas chromatography instrument has a first end in fluid communication with an inlet of the respective gas chromatography instrument, and a second end in fluid communication with the detector of the respective gas chromatography instrument.

Also disclosed are gas chromatography instruments for analyzing at least one constituent compound of a sample, wherein a rate controller of a gas chromatography instrument comprises at least one temperature sensor. In one aspect, the rate controller selectively signals the valve of the rate controller to discharge the fluid through the lumen of the tube. In another aspect, the rate controller is configured to control a temperature of the fluid in the lumen of the tube. In a further aspect, the rate controller is configured to control an amount of time that an electric current is passed to the heating element.

Reference will now be made in detail to the present preferred embodiment(s) of the invention, examples of which are illustrated in the accompanying drawings. Wherever possible, the same reference numbers are used throughout the drawings to refer to the same or like parts.

Figure 2:
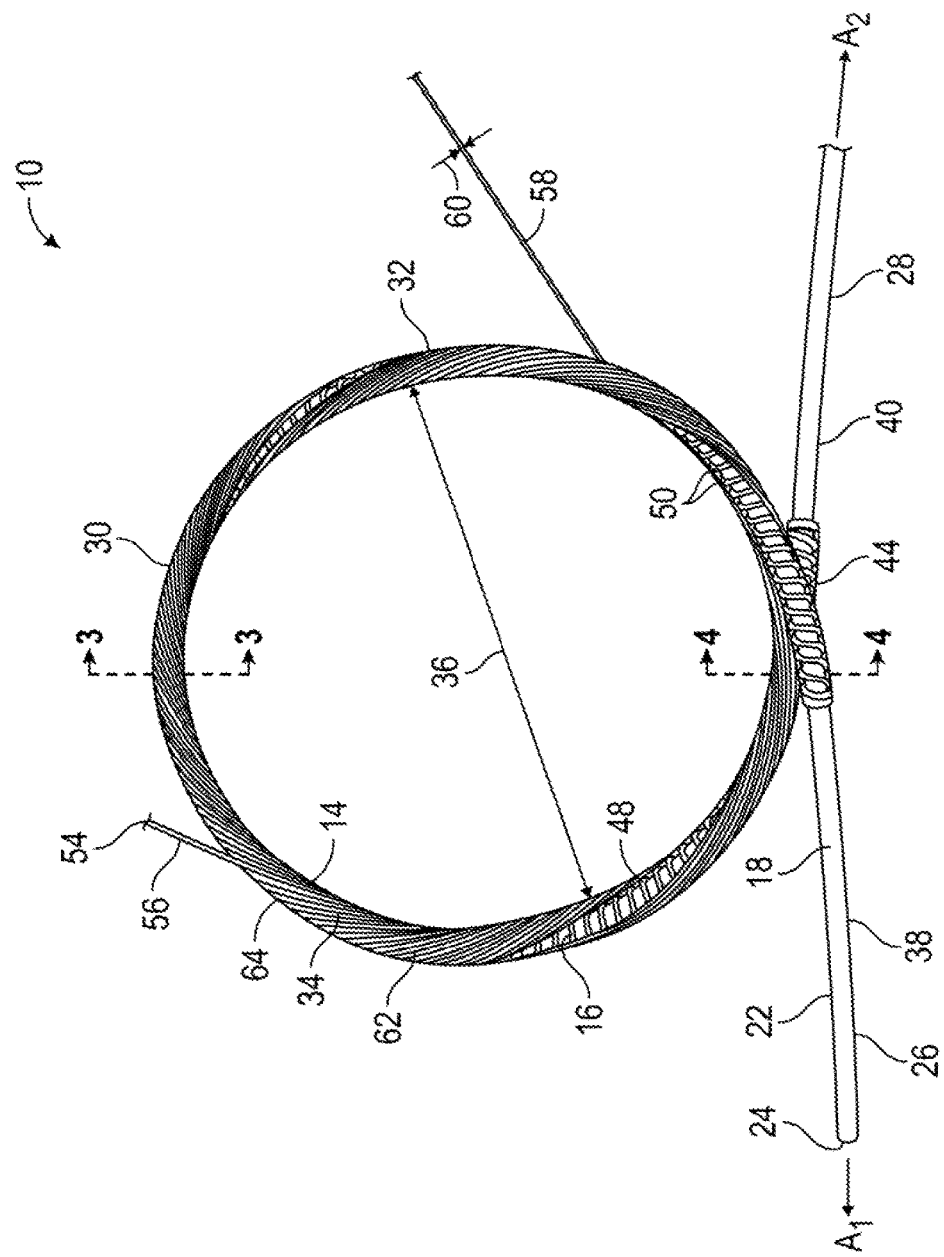
FIG. 2 is a side elevational view of a column assembly, according to one aspect.

According to various embodiments, and as illustrated in FIGS. 1 and 2, a column assembly 10 for a gas chromatography instrument 12 is provided. The column assembly can be cooled by a fluid such that the temperature and/or the rate of change of temperature of a capillary column 14 (and an analyte contained in the capillary column) can be controlled. In one aspect, the column assembly 10 comprises the capillary column 14, a heating element 16, and a tube 18. In another aspect, the tube can be positioned relative to the capillary column and the heating element such that as a cooling fluid is passed through the tube, the temperature of both the capillary column and the heating element can be reduced.

In one exemplary embodiment, the heating element 16 can be positioned in contact with at least a portion of the capillary column 14. The tube 18 can be positioned in contact with at least a portion of the heating element 16 and/or the capillary column 14. A fluid, such as a cryogenic liquid, liquid nitrogen and the like, or a chilled liquid such as chilled water or ethylene glycol and the like can flow from a pressurized fluid source 20 through a throttling device 70 and into the tube 18. Heat contained in the capillary column 14 (and the analyte contained therein) can be transferred directly or through the heating element 16 to the fluid in the tube 18, thereby lowering the temperature of at least a portion of the capillary column 14.

Figure 3:
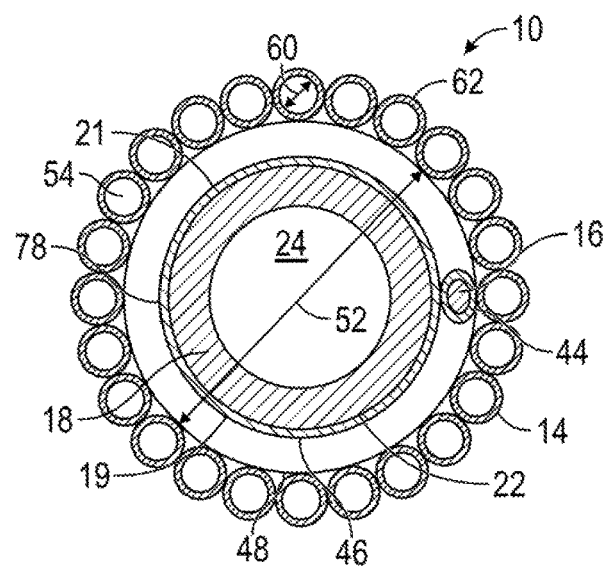
FIG. 3 is a cross-sectional view of the column assembly of FIG. 2, taken along line 3-3 of FIG. 2.

Referring now to FIG. 2, the tube 18 can be an elongate tube having an exterior surface 22. In one aspect, the exterior surface of the tube can surround and define a lumen 24 configured for receiving the fluid therein, as illustrated in FIG. 3. The tube can be formed from a material having a high thermal conductivity, such as aluminum, or using thin walls with a more moderate thermal conductivity such as stainless steel and the like. In one example, the tube can be aluminum tubing having a suitable outer diameter (for example, 1/16th inch).

According to one aspect, the tube 18 can have a first end 26, a second end 28, and a central portion 30 extending between the first and second ends. The central portion 30 of the tube 18 can be formed into an arcuate shape 32 having a predetermined radius. In one aspect, the central portion of the tube can be formed into a loop shape 34, such that, when viewed from the side as in FIG. 2, the central portion 30 of the tube 18 can be substantially circular in shape. In one example, the loop shape can have an inner diameter 36 of between about 1 inch and 12 inches. In another example, the loop shape 34 can have an inner diameter of between about 2 inches and 5 inches. In another example, the loop shape can have an inner diameter 36 of about 2.5 inches. Alternatively, it is contemplated that the central portion of the tube 18 can be formed into a loop shape, such that when viewed from the side, the central portion 30 of the tube appears to be substantially oval or any other shape.

Figure 4:
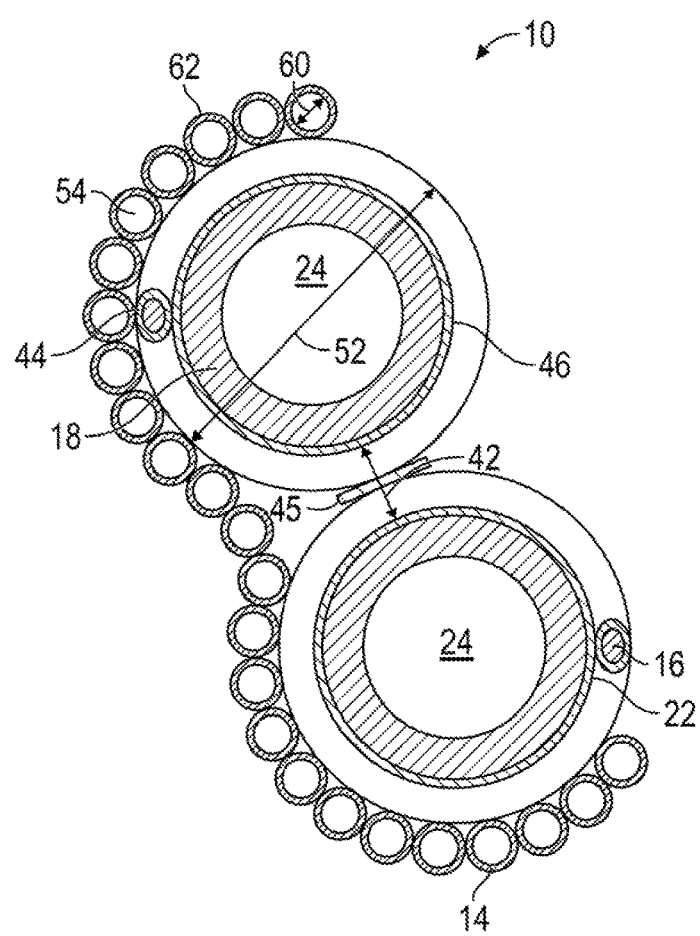
FIG. 4 is a cross-sectional view of the column assembly of FIG. 2, taken along line 4-4 of FIG. 2.

In one aspect, the first end 26 and the second end 28 of the tube 18 can be substantially parallel to each other. In an example, at least a first portion 38 of the first end of the tube can be positioned along a first axis $A_1$, and at least a second portion 40 of the second end of the tube 18 can be positioned along a second axis $A_2$ that is substantially parallel to the first axis. In another example, at least the first portion 38 of the first end of the tube can be positioned at an obtuse angle relative to the second end of the tube. In one embodiment, at least a portion of the first end of the tube can overlie the second end of the tube 18. As can be seen in FIG. 4, in this embodiment, the first end 26 and the second end 28 of the tube can be spaced from each other a predetermined tube distance 42. In one example, the predetermined tube distance can be zero so that the exterior surface 22 of the first end of the tube and the exterior surface of the second end of the tube 18 are in contact with each other. In one aspect, at least a portion of the first end 26 of the tube can be substantially parallel to and overlie the second end 28 of the tube 18.

With reference again to FIG. 2, the heating element 16 can be an elongated electrical resistant heating wire, such as, for example and without limitation, a nickel alloy resistance wire. In one aspect, the heating element can be a conventional heating wire. For example, the heating wire can be a nickel alloy #875 heating wire having a suitable diameter (e.g., 0.008 inches). As known to one of skill in the art, the heating element can comprise an insulating layer 44 to prevent electrical shorts. It is contemplated that the heating element 16 can be wrapped with an insulating layer 44, such as, for example and without limitation, 600 denier Nextel 312 roving from 3M Ceramics, as described in U.S. Pat. No. 6,490,852.

In another aspect, one or more electrically insulating layers can be positioned between electrically conductive components such as the heating element 16, the tube 18, and the like. In this aspect, a thin layer of a non-electrically conducting material can provide electrical insulation and sufficient thermal conduction for rapid heat transfer between the elongate wire, tube, and the capillary column 14.

In one embodiment, optionally, a thin layer of insulation can surround the exterior surface 22 beneath where the heating element 16 will be wound onto the tube. As illustrated in FIG. 3, it is contemplated that at least a portion of the tube 18 can be wrapped with an insulating layer 19, such as, for example and without limitation, 600 denier Nextel 312 roving. The heating element, with or without the insulating layer 44, can be positioned in contact with at least a portion of the exterior surface 21 of the insulating layer surrounding the tube 18. As can be seen in FIG. 3 and described more fully below, when positioned in contact with the tube or the insulating layer surrounding the tube, the heating element 16 can have a first surface 46 directed toward the exterior surface of the tube 18, and an opposed second surface 48 directed away from the exterior surface 22 of the tube. For clarity and conciseness, when used herein, reference to the tube 18 can refer to the tube with or without the presence of the insulating layer surrounding the tube. For example, reference to the exterior surface 22 of the tube can refer to the exterior surface of the tube, or to the exterior surface of the insulating layer surrounding the tube 18.

In one aspect, the heating element 16 may comprise the tube 18. For example, if the tube is a metallic tube, the tube 18 can be resistively heated by the conduction of electricity through the length of the tube so that a separate heating element would not be required.

In accordance with some embodiments of the invention, the capillary column 14 may comprise a metal clad capillary column (i.e., a metal coating on the capillary column), in which the metal coating is capable of providing resistive heating—i.e., heat is generated when electric current is passed through the metal coating. In these embodiments, there is no need to provide a separate heating element. In other words, the heating element may comprise the meal coating on the capillary column.

With reference again to FIG. 2, the capillary column 14 can be a conventional, elongate capillary column defining a conduit 54 and having a front end 56, a rear end 58 and a column diameter 60.

In order to assemble the column assembly 10, the tube 18 can be formed into a desired shape. In an example, and as illustrated in FIG. 2, the tube can be formed into the loop shape 34 having first and second ends 26, 28 positioned such that at least a portion of the first and second ends are substantially parallel to each other and adjacent or near each other. It is of course contemplated that the tube can be formed into other shapes. For example, it is contemplated that at least portions of the tube 18 can be substantially straight or arcuate.

The capillary column 14 and the heating element 16 can be positioned relative to the tube 18 such that as cooling fluid is passed through the tube, the temperature of both the capillary column and the heating element can be reduced. In one aspect, the capillary column 14 and the heating element 16 can be wound around the tube 18. In a further aspect, the capillary column 14 and the heating element can be helically wound around the tube 18. It is contemplated that at least a portion of the capillary column 14, at least a portion of the heating element, or at least portion of both the capillary column and the elongate wire can be in contact with the exterior surface 22 of the tube 18. In another aspect, and as illustrated in FIG. 2, the heating element 16 can be coiled around the tube, and the capillary column 14 can be wound around the combination of the heating element and the tube. Alternatively, the capillary column can be wound around the tube 18, and the heating element 16 can be coiled around the combination of the capillary column and the tube.

In an exemplary embodiment, the tube 18 can be formed into the loop shape. The heating element 16 can be coiled around at least a portion of the exterior surface 22 of the tube 18. In one aspect, the heating element can be helically coiled around the exterior surface of at least a portion (e.g., the central portion 30) of the tube. In this aspect, when the heating element 16 is helically coiled around at least a portion of the exterior surface 22 of the tube 18, a plurality of coils 50 can be formed such that each coil of the heating element 16 is adjacent at least one other coil 50. In this manner, the heating element can be formed to provide substantially uniform coverage over the exterior surface of the tube that has only small and substantially uniform gaps between coils of the heating element 16. In one aspect, if a portion of the first end 26 of the tube overlies the second end 28 of the tube, an insulating layer 45 such as, for example and without limitation, a sheet of Nextel Flame Stopping Dot Paper 312 from 3M Ceramics can be positioned between the first and second ends of the tube 18 to prevent contact between the heating element positioned adjacent the first end of the tube and heating element positioned adjacent the second end of the tube as illustrated in FIG. 4.

With reference to FIG. 2, in one aspect, the heating element can be coiled around the exterior surface of the tube with a predetermined pitch (i.e., number of coils of the heating element per inch of tube). In another aspect, the pitch of the heating element 16 can be between about 10-30 coils of the heating element per inch of tube. For example, the tube 18 can be put into a winding machine, and the heating element 16 can be coiled around at least a portion of the exterior surface 22 of the tube at a desired pitch.

In this embodiment, at least a portion of the capillary column can be positioned in contact with at least a portion of the second surface 48 of the heating element 16. In one aspect, the capillary column 14 can be wound around at least a portion of the second surface of the heating element. For example, the capillary column can be helically wound around at least a portion of the second surface 48 of the heating element. In this aspect, the capillary column 14 can be wound around at least a portion of the second surface 48 of the heating element 16 such that a peripheral surface 62 of each winding 64 of the capillary column can be adjacent to and/or in contact with the peripheral surface of another winding. In this manner, a capillary column having a predetermined length can be helically wound around at least a portion of the second surface 48 of the heating element 16. In one example, the predetermined length of the capillary column can be between about 1 meter and about 20 meters. In another example, the predetermined length of the capillary column 14 can be between about 3 meters and about 15 meters. In another example, the predetermined length of the capillary column can be about 5 meters.

In one aspect, the capillary column can be wound around the second surface 48 of the heating element 16 with a predetermined pitch (i.e., number of windings of the capillary column per inch of tube). In another aspect, the pitch of the capillary column 14 can be between about 0.2-0.5 windings of the capillary column per inch of tube. The pitch of the capillary column can be selected so that the capillary column is arranged in an ordered layer on the second surface 48 of the heating element. In one embodiment, the pitch of the coils 50 of the heating element 16 can be greater than the pitch of the windings 64 of the capillary column 14. Alternatively, the pitch of the heating element can be equal to or less than the pitch of the capillary column.

With reference to FIGS. 3 and 4, after coiling the heating element 16 around at least a portion of the exterior surface 22 of the tube 18, each coil 50 of the heating element can have a coil diameter 52. In one aspect, a ratio of the coil diameter 52 to the column diameter 60 can be about 1-1, about 5-1, about 10-1, about 15-1, about 20-1, about 25-1, about 30-1, or greater than about 30-1. As the column diameter 60 decreases, more of the peripheral surface 62 of the capillary column 14 can be in proximity to the second surface 48 of heating element 16, and the more efficiently heat can be transferred between the capillary column and the heating element.

Figure 5:
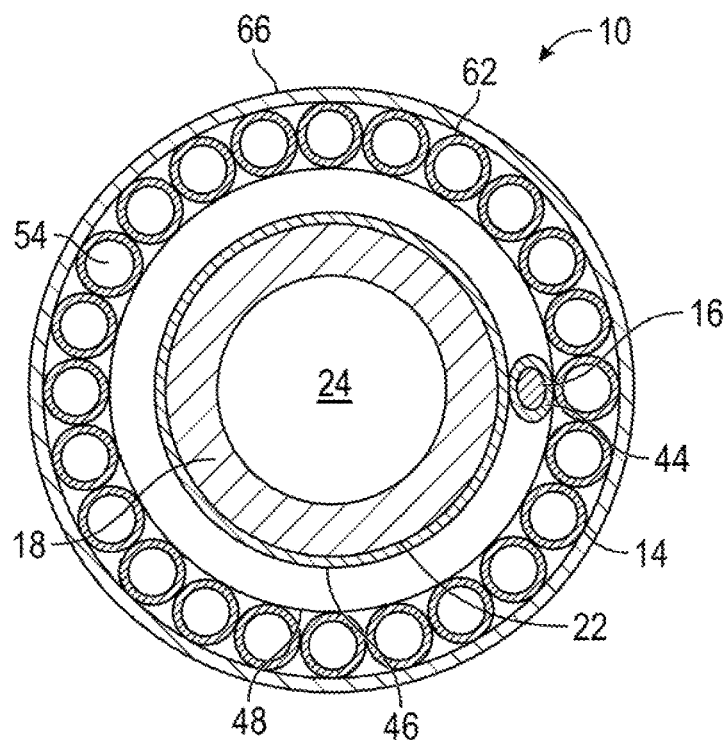
FIG. 5 is a cross-sectional view of the column assembly of FIG. 2 having a sheath, according to one aspect.

As illustrated in FIG. 5, after the capillary column 14 has been positioned on the heating element 16, at least a portion of the column assembly 10 can be at least partially surrounded by a sheath 66, such as for example and without limitation, at least one layer of metallic foil. The sheath can be wrapped around at least a portion of the column assembly 10 to hold in heat and to help achieve a uniform heating of the capillary column 14.

Figure 6:
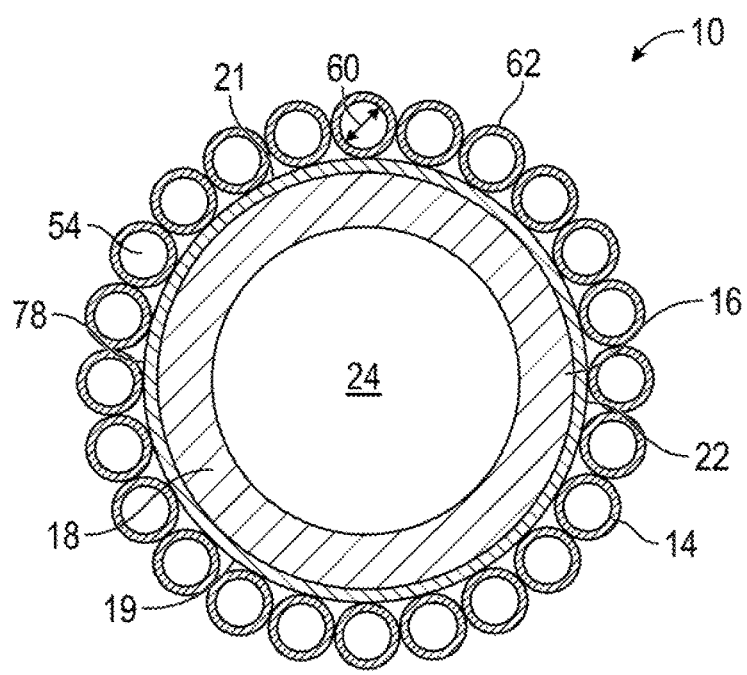
FIG. 6 is a cross-sectional view of a column assembly, according to one aspect.

As noted above, in some embodiments, the heating element may be the coating on the capillary column or the heating element may be the tube 18 that can produce heat when currents are passed through the tube. In these embodiments, there is no separate heating element, and one may simply wrap (coil) the capillary column (coated or not) around the tube 18, as illustrated in FIG. 6. With such embodiments, one may put an insulation on the metal coated capillary column (optionally also on the tube 18), or one may put an insulation on the tube 18 (and optionally also on the capillary column, with or without a metal coating), before coiling the capillary column around the tube 18.

Thus, in one aspect, the capillary column 14 can be positioned in contact with at least a portion of the exterior surface 22 of the tube 18. In another aspect, the capillary column 14 can be wound around at least a portion of the exterior surface of the tube. In another aspect, the capillary column can be helically wound around at least a portion of the exterior surface 22 of the tube. In still another aspect, the capillary column 14 can be wound around at least a portion of the exterior surface 22 of the tube such that the peripheral surface 62 of each winding of the capillary column can be adjacent to and/or in contact with the peripheral surface of another winding. In this manner, a capillary column having a predetermined length can be helically wound around at least a portion of the exterior surface 22 of the tube. According to this aspect, the pitch of the capillary column 14 can be between about 0.2-0.5 windings of the capillary column per inch of tube. In another aspect, when the tube 18 is coupled to a pressurized source of fluid, as described more fully below, all gas flow connections to the tube can be made with electrically-insulating components.

The above examples describe wrapping (coiling) the capillary column 14 (and the heating element 16, if present) around the tube 18. While this is more practical, one skilled in the art would appreciate that one may also wrap the tube 18 around the capillary column 14 (with or without a separate heating element) without departing from the scope of the invention.

With reference to FIG. 1, after the column assembly 10 has been assembled, the column assembly can be used to control the temperature and/or the rate of change of temperature of the capillary column 14 and an analyte contained therein the column. In use, in order to raise the temperature of the capillary column and the analyte contained therein, the heating element 16 can be energized such that the heating element emits heat. This heat can be transferred through conduction to the capillary column 14, thereby raising the temperature of the capillary column and the analyte contained therein. In another aspect, the temperature of the capillary column 14 can be raised to a predetermined temperature at a predetermined rate. For example, the temperature of the capillary column can be raised at a rate of between about 0° C. and 50° C. per second.

The temperature of the capillary column can be lowered by flowing a fluid, such as for example and without limitation, a cryogenic liquid, through the lumen 24 of the tube 18. For example, after the heating element has raised the temperature of the capillary column 14 to a desired temperature for a desired length of time, the temperature of the capillary column can be lowered by flowing a cryogenic liquid through at least a portion of the lumen of the tube 18. Evaporative cooling and the Joule-Thomson cooling effect can both be occurring from the cryogenic liquid evaporation and vapor expansion in the tube 18. Heat contained in the capillary column and the analyte contained therein can be transferred through the heating element 16 to the fluid in the tube 18, thereby lowering the temperature of the capillary column 14. In one aspect, the temperature of the capillary column 14 can be lowered to a predetermined temperature at a predetermined rate. For example, the temperature of the capillary column can be lowered at a rate of between about 0° C. and 200° C. per second. In another example, the temperature of the capillary column 14 can be lowered at a rate of between about 0° C. and 150° C. per second, between about 0° C. and 120° C. per second, or between about 0° C. and 100° C. per second. In another example, the temperature of the capillary column can be lowered at a rate of about 82° C. per second. In another aspect, the temperature of the capillary column 14 can be lowered to a predetermined temperature at a variable rate. In still another aspect, the temperature of the capillary column can be lowered to a predetermined temperature at a plurality of predetermined rates. For example, the temperature can be lowered at a first rate for a first amount of time, a second rate for a second amount of time, a third rate for a third amount of time, and so on.

It is also contemplated that the temperature of the capillary column 14 can be adjusted by simultaneously activating both the heating element 16 and the flow of the fluid through the tube 18. Thus, the heating element can emit heat, and the cooling fluid can remove heat from the capillary column 14 simultaneously. In one aspect, the temperature of the capillary column 14 can be adjusted by heating with the heating element 16, turning on the flow of cooling fluid when the capillary column reaches a predetermined temperature, and controlling both the heating element 16 and the flow of the fluid to maintain the temperature of the capillary column in a pre-determined range. In another aspect, in order to achieve subambient temperature, it is contemplated that the temperature of the capillary column 14 can be adjusted by turning on the flow of cooling fluid until a subambient temperature in the capillary column 14 is reached, and then heating with the heating element as necessary to maintain the column temperature in a predetermined range. In still another aspect, because the control of the cooling of the column may not provide the finesse of heating control, it is contemplated that a timed pulse of cooling can be used, with or without energizing the heating element, to control the temperature of the capillary column 14.

As illustrated in FIG. 1, in one aspect, the column assembly can further comprise the throttling device 70 positioned in fluid communication with the lumen 24 of the tube 18. The throttling device can comprise at least one of an orifice, a frit or a valve. In one aspect, the throttling device 70 can be used to alter the pressure and/or flowrate of the fluid in the lumen of the tube. For example, the throttling device can control the Joule-Thomson effect of the fluid by allowing the fluid to expand a predetermined amount after passing through the throttling device 70. In another aspect, the throttling device 70 can control the rate of evaporative cooling by controlling the flowrate of cryogenic fluid to the tube. It should be noted that, in one aspect, a throttling device could not be needed if the fluid in the tube is, for example, liquid nitrogen. In one aspect, the flowrate of fluid in the tube can be a substantially constant flowrate. In another aspect, the flowrate of fluid in the tube 18 can be varied, such as would occur if, for example, the fluid was released from the source in pulses.

The throttling device can be placed in fluid communication with the first end 26 of the tube 18, such that fluid can flow from the pressurized fluid source 20 through the throttling device 70 and into the lumen 24 of the tube.

The column assembly 10 can further comprise at least one sensor 72 for measuring pressure and/or flowrate of the fluid. In one aspect, the at least one sensor can be positioned downstream of the throttling device such that pressure and/or flowrate of the fluid can be measured after passing through the throttling device 70. The measured pressure and/or flowrate of the fluid can be sent to a display so that a user can manually adjust the throttling device until a desired pressure and/or flowrate of the fluid has been achieved. In one example, the at least one sensor 72 can be coupled to a rate controller 74 (described more fully below), and the measured pressure and/or flowrate of the fluid can be sent to the rate controller to allow for an automated adjustment of the throttling device 70 until a desired pressure and/or flowrate of the fluid has been achieved.

In one aspect, the column assembly 10 can further comprise at least one temperature sensing device 78, illustrated in FIGS. 1 and 3. The temperature sensing device can be a thermocouple, such as, for example and without limitation, a type K thermocouple. According to various aspects, the at least one temperature sensing device 78 can be placed between the coils 50 of the heating element 16 and the tube 18, and/or between the coils of the heating element and the windings 64 of the capillary column 14. In another aspect, the temperature sensing device can be placed in different locations in order to provide varying ability to control the temperature of the capillary column 14. For example, the temperature sensing device 78 can be positioned between the tube and the heating element. In another example, the temperature sensing device can be positioned in proximity to the capillary column. In another aspect, the temperature sensing device 78 can be located with the windings of the capillary column 14. Thus, the temperature sensing device can be used to measure the temperature of the peripheral surface 62 of the capillary column and/or the contents of the capillary column 14. In another aspect, the temperature sensed by the at least one temperature sensing device 78 can be sent to a display so that a user can manually monitor the temperature of the capillary column. In still another aspect, the sensed temperature can be signaled to the rate controller 74 to allow for an automated adjustment of the throttling device 70, the heating element 16 and/or a fluid source valve 82. The temperature sensing device can be held in place with an adhesive, such as, for example and without limitation, silicone RTV glue.

In one aspect, the column assembly 10 can further comprise at least one supplemental heater. The at least one supplemental heater can be configured such that at least a portion of the capillary column 14 can be heated with the at least one supplemental heater so that the temperature of portions of the column not positioned adjacent the heating element 16 can be controlled. For example, a portion of the front end 56 and the rear end 58 of the column that couples the column assembly 10 to the gas chromatography instrument 12 can be heated with at least one supplemental heater to limit the development of unheated "cold spots" in the column. It is of course contemplated that the at least one supplemental heater could be coupled to the rate controller 74 and at least one temperature sensing device 78 so that the rate controller can control the at least one supplemental heater.

The column assembly 10 can be used with a gas chromatography instrument 12 for controlling a rate of change of temperature of the capillary column. In one aspect, a gas chromatography instrument 12 can comprise the throttling device 70, the pressurized fluid source 20 of pressurized fluid, a detector 68 for analyzing the at least one constituent compound, and the rate controller 74.

The pressurized fluid source 20 of pressurized fluid can be a conventional source of pressurized fluid having a fluid source valve 82 configured to start and stop the flow of fluid from the pressurized source of fluid.

In one aspect, the rate controller 74 comprises a processor 76. The rate controller can be coupled to at least one of the heating element 16, the at least one temperature sensing device 78, the throttling device 70, and the fluid source valve 82. The rate controller 74 can be configured to control the temperature and/or the rate of change of temperature of the capillary column 14 until a desired temperature and/or the rate of change of temperature of the capillary column has been achieved. For example, the temperature sensed by the at least one temperature sensing device 78 can be sent to the processor 76 to allow for automatic control of the temperature and/or the rate of change of the temperature of the capillary column. In another example, the measured pressure and/or flowrate of the fluid sensed by the at least one sensor 72 can be sent to the processor 76 to allow for automatic control of the temperature and/or the rate of change of the temperature of the capillary column 14.

In another example, the rate controller 74 can selectively signal the fluid source valve 82 to discharge fluid from the pressurized fluid source 20 of pressurized fluid to the lumen 24 of the tube 18. Upon discharge of the fluid through the lumen of the tube, heat can be transferred from the capillary column 14 to the fluid, thereby lowering the temperature of the capillary column. In another aspect, the rate controller 74 can be coupled to the heating element 16 and can be configured to control the duty cycle of the voltage to the heating element and/or to control the voltage or electric current to the heater. In still another aspect, the rate controller 74 can be configured to control an amount of time that an electric current is passed to the heating element. Thus, in one aspect, the rate controller can be configured to control the temperature and/or the rate of change of temperature of the capillary column 14 by controlling both the heating element 16 and the flow of fluid through the lumen 24 of the tube 18.

As illustrated in FIG. 1, the capillary column 14 can be coupled to a gas chromatography instrument 12 by conventional means. For example, the front end 56 of the capillary column of the column assembly can be in fluid communication with a sample inlet of the gas chromatography instrument 12 for introducing a sample into the front end of the capillary column, and a carrier gas inlet of the gas chromatography instrument 12 for introducing a carrier gas into the front end of the capillary column. The rear end 58 of the capillary column can be in fluid communication with the detector 68 of the gas chromatography instrument 12. The lumen 24 of the first end 26 of the tube 18 can be placed in fluid communication with the pressurized fluid source 20, and the second end 28 of the tube 18 can be vented to the atmosphere to exhaust the fluid after it is discharged from the tube. The throttling device 70 can be positioned in fluid communication with the lumen 24 of the tube and the pressurized fluid source 20 of pressurized fluid.

To use the gas chromatography instrument 12, an analyte can be introduced into the capillary column 14. The temperature of the capillary column and/or the analyte in the column can be adjusted by the column assembly 10. In one aspect, the temperature can be adjusted by activating the heating element 16, the flow of the fluid through the tube 18, and/or some combination of both. The heating element can be activated and/or the fluid source valve 82 can be activated to discharge fluid from the pressurized fluid source 20 of pressurized fluid through the tube based on a desired column temperature setpoint, the actual temperature of the column, and/or the ambient temperature. In one aspect, a control algorithm can be executed by the rate controller 74 and/or the processor 76 to determine which elements to activate depending in part on the size of the difference between the desired column temperature setpoint and the current temperature, and further on the sign of the deviation (i.e., does the temperature of the capillary column 14 need to be raised or lowered).

The heating element 16 can be energized, either manually by a user or automatically as signaled by the rate controller 74. In one aspect, heat emitted by the heating element can be transferred to the capillary column 14 and the analyte, and the heating element 16 can remain energized until a desired temperature has been achieved for a desired period of time. In another aspect, the heating element 16 can remain energized for a pre-determined period of time. In a typical GC run, the temperatures of the capillary column 14 may be programmed to reach the desired temperatures at the selected times, by controlling the rates of heating.

When it is desired to lower the temperature of the capillary column 14, the fluid can be discharged from the pressurized fluid source 20 of pressurized fluid through the fluid source valve 82 and the throttling device 70 and into the lumen 24 of the tube 18. When the pressurized fluid flow through the throttling device 70, the fluid expands and cools due to Joule-Thomson effects. As the cooled fluid flows through the tube, heat can be transferred from the capillary column 14 to the fluid. The at least one sensor 72 and the at least one temperature sensing device 78 can provide feedback to the rate controller 74 so that the rate controller 74 can automatically control the temperature and/or the rate of change of temperature of the capillary column, by adjusting at least one of the fluid source valve 82, the throttling device 70, and the heating element 16. For example, the rate controller can control the temperature of the capillary column so that the temperature of the capillary column 14 can decrease at a rate of about 82° C. per second.

In one aspect, when the heating element 16 comprises the tube 18 and the capillary column 14 is helically wound around the tube, the temperature of the capillary column can be adjusted by heating the tube and/or flowing the cooling fluid through the tube.

Examples

Embodiments of the invention allow for quick temperature equilibration of a capillary GC column assembly. Therefore, fast cycles may be used for analysis. The following examples demonstrate the utilities and advantages of the embodiments of the invention.

In these examples, a mixture of test samples. EPA TO-14 Calibration Mix from Sigma Aldrich Co. (St. Louis, Mo.), is used. This mixture contains 39 components of toxic organic compounds that might be found in ambient air. This mixture is typically used to calibrate GC-MS equipment that is used for monitoring ambient air for volatile organic chemicals, according to the standard TO-14 or TO-14a method (Compendium of Methods for Determination of Toxic Organic Compounds in Ambient Air, Second Edition, EPA/625/R-96/010b, January 1999).

Figure 7:
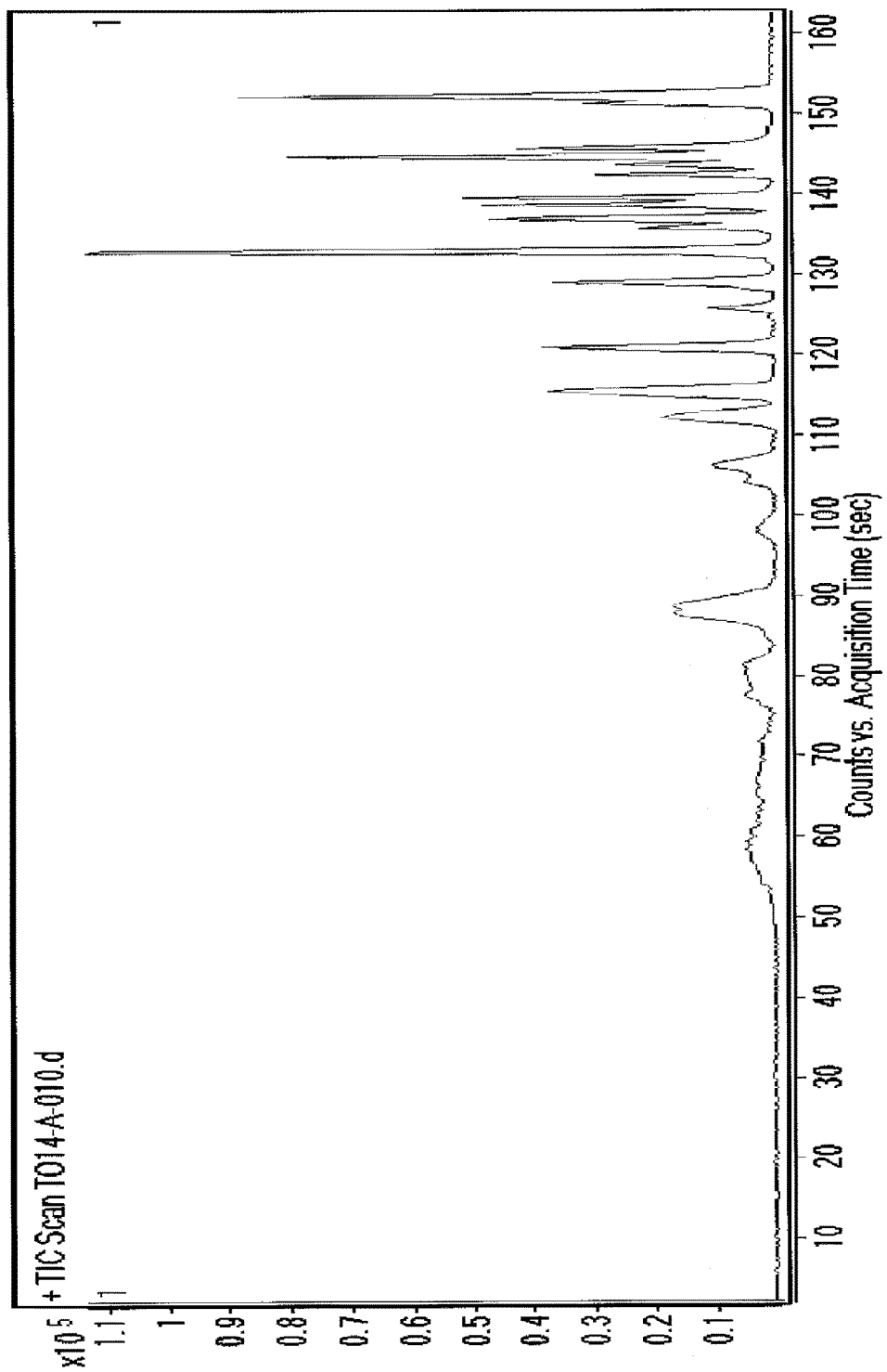
FIG. 7 shows a typical separation of a standard mixture using a fast cooling low thermal mass (LTM) column assembly in accordance with one embodiment of the invention.

FIG. 7 shows results of a GC run using the TO-14 mixture. The graph shows the total ion currents (TIC) as a function of time, as monitored by a time-of-flight mass spectrometer connected to a GC. The testing was performed using valve injection from a 1 μL gas sample loop. A 1 ppm gas standard TO-14 mix was used to fill the gas sample loop. A fast cooling low thermal mass (LTM) assembly in accordance with embodiments of the invention was used to analyze the mixture. Detection was done using an Agilent quadrapole-time of flight mass spectrometer. The fast cooling LTM assembly was connected to the sample valve and the detector using fused silica capillary tubing.

FIG. 7 shows a typical separation of the TO-14 mix using the fast cooling LTM assembly in accordance with embodiments of the invention. The fast cooling LTM assembly used in this example was built using a 5 m×0.25 mm×1 μm DB-5 column (Agilent Technologies). The DB-5 columns contain (5%-phenyl)-methylpolysiloxane and are non-polar general purpose columns used in a wide range of applications. This column is equivalent to the USP Phase G27 GC column.

In the test shown in FIG. 7, the starting temperature was sub-ambient at 0° C. The temperature program for the fast cooling LTM assembly was as follows: 0° C. for 30 s, then 0° C. to 80° C. at 60° C./min, followed by 80° C. to 240° C. at 300° C./min, followed by 240° C. for 15 s. The temperature ramping is by controlling the heating element using the controller of the GC equipment. This temperature program takes 2.61 min. Using an LTM assembly of the invention, the cooling process takes only a few seconds after the run. In fact, one only needs approximately 15-20 s for the system temperature to stabilize prior to the next sample introduction. In other words, embodiments of the invention allows for relatively fast recycling of the equipment. This is validated in the experiments shown in FIG. 8.

Figure 8:
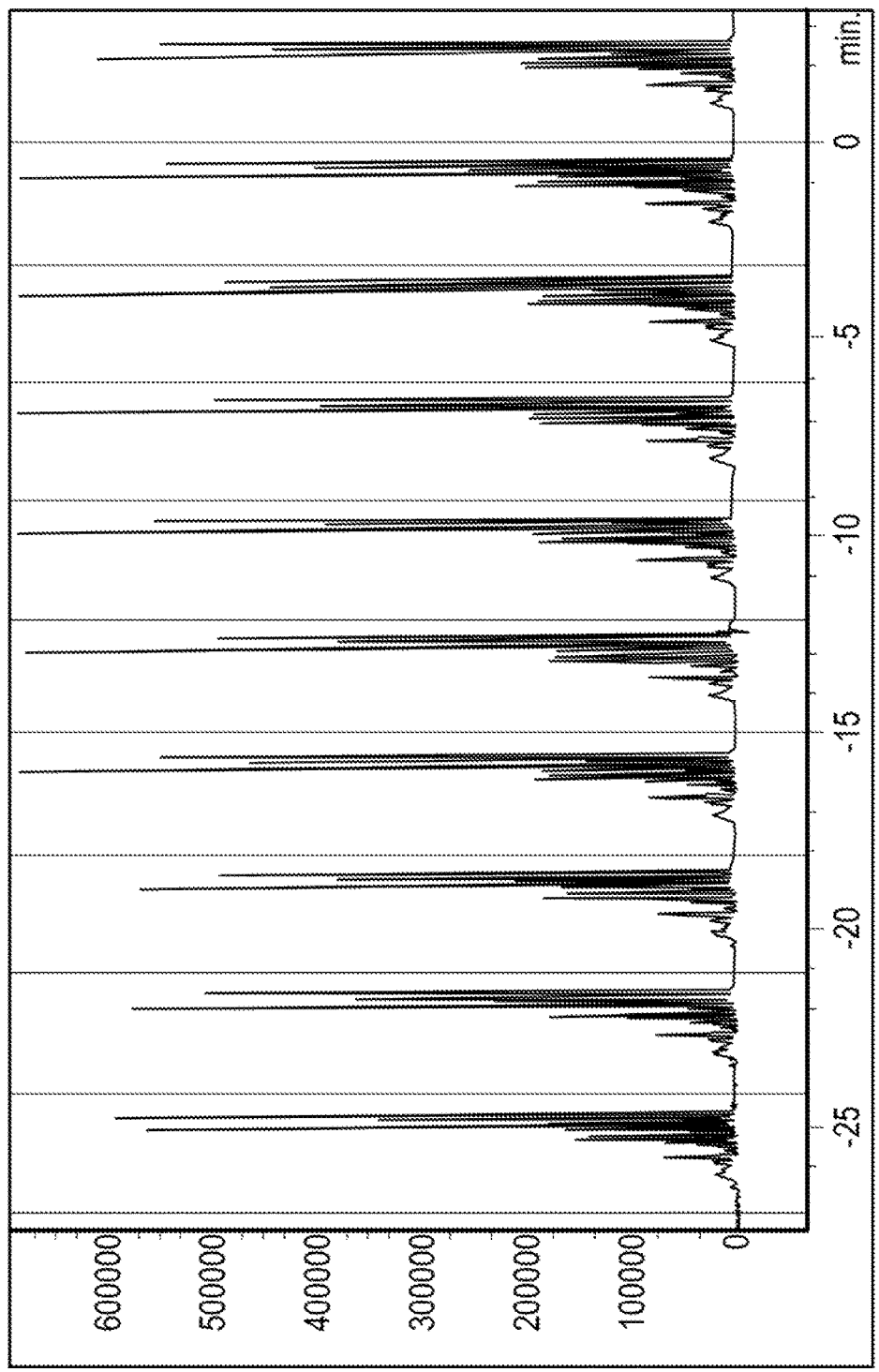
FIG. 8 shows quick recycle times for a fast cooling low thermal mass (LTM) column assembly such that experiments can be repeated without long delays (e.g., 3 minutes shown here) in accordance with embodiments of the invention.

FIG. 8 shows results of automatic repetitions of the analysis described in FIG. 7—i.e., with the same test mixture and the same temperature ramping profiles. In these repetitive experiments, the sample introductions and analyses were performed every 3 minutes. As shown in FIG. 8, even with only 3-minute cycle times, the results are very reproducible, suggesting that the system has cooled and stabilized before the next run. In other words, about 20 s cooling and equilibrium time was sufficient to reestablish stable conditions between the runs. These results attest to the utility and advantages of embodiments of the invention.

The ultrafast (e.g., about 20 s) cooling and equilibrium time shown in FIG. 8 is quite impressive, as compared with a typical GC system, for which several minutes of cooling and equilibrium are often required. For example, for a standard laboratory GC system (such as the Agilent 7890 GC), it will take about 4-5 minutes using liquid nitrogen as a coolant or 5-6 minutes using liquid $CO_2$ as a coolant to cool the column down from 240° C. to 0° C. In addition, it would require a large amount of cryogen to cool an oven of a typical laboratory GC system, and, therefore, the cryogen is typically applied only after the temperature has cooled to about 50° C. in order to conserve the cryogen. The 4-6 minute cooling times are significantly longer than the about 20 s cooling time of an LTM column assembly in accordance with embodiments of the invention.

In addition to slower cooling, a standard laboratory GC also cannot heat as fast as an LTM assembly. In particular, it would be difficult to achieve a heating rate of 300° C./min with a standard laboratory GC system. In contrast, an LTM column assembly in accordance with embodiments of the invention not only cools fast, but also heats up fast.

Although several embodiments of the invention have been disclosed in the foregoing specification, it is understood by those skilled in the art that many modifications and other embodiments of the invention will come to mind to which the invention pertains, having the benefit of the teaching presented in the foregoing description and associated drawings. It is therefore understood that the invention is not limited to the specific embodiments disclosed herein, and that many modifications and other embodiments of the invention are intended to be included within the scope of the invention. Moreover, although specific terms are employed herein, they are used only in a generic and descriptive sense, and not for the purposes of limiting the described invention.

What is claimed is:

1. A column assembly for gas chromatography, comprising:
   a capillary column comprising a front end and a rear end; and
   a tube having an exterior surface and defining a lumen, wherein the tube is configured for receiving a pressurized cooling fluid, and wherein the capillary column is disposed around the tube such that when the pressurized cooling fluid is passed through the lumen of the tube, a temperature of the capillary column is reduced.

2. The column assembly of claim 1, wherein the capillary column comprises a metal coating on an outer surface.

3. The column assembly of claim 1, wherein the tube is made of a metal.

4. The column assembly of claim 3, wherein the capillary column is helically wound around the tube.

5. The column assembly of claim 1, further comprising a throttling device in fluid communication with the lumen of the tube.

6. The column assembly of claim 5, wherein the throttling device comprises a valve.

7. The column assembly of claim 5, wherein the throttling device comprises a frit.

8. The column assembly of claim 1, further comprising an insulating layer surrounding at least a portion of the tube.

9. A gas chromatography instrument, comprising:
the column assembly of claim 1;
a sample inlet for introducing a sample into the front end of the capillary column; and
a detector in fluid communication with the rear end of the capillary column.

10. A method for manufacturing a gas chromatography column assembly, the method comprising:
providing a capillary column, the capillary column comprising a metal coating on air outside surface thereof; and
disposing the capillary column around a tube such, that when a cooling fluid flows through a lumen of the tube, a temperature of the capillary column is reduced.

11. The method of claim 10, further comprising: wrapping a heating element around at least one of the capillary column and the tube.

12. The method of claim 10, wherein the capillary column is arranged such that it wraps around the tube.

13. The method of claim 10, further comprising connecting a throttling device with one end of the tube such that the throttling device is in fluid communication with the tube.

14. The method of claim 13, wherein the throttling device comprising a valve or a frit.

15. A method, comprising:
heating a capillary column to cause a temperature increase of an analyte in the capillary column with a heating element adjacent to the capillary column; and
passing a cooling fluid through a tube which both the capillary column and the heating element are disposed around, to maintain or lower the temperature of the capillary column and the heating element.

16. A column assembly for gas chromatography, comprising:
a capillary column comprising a front end and a rear end;
a heating element arranged in contact with at least a portion of the capillary column, or a portion of the tube, or both; and
a tube having an exterior surface and defining a lumen, wherein the tube is configured for receiving a pressurized cooling fluid through the lumen, and wherein the capillary column is disposed around the tube such that when the pressurized cooling fluid is passed through the lumen of the tube, a temperature of the capillary column is reduced.

17. The column assembly of claim 16, wherein the heating element comprises an elongate wire, and wherein the capillary column and the elongate wire are helically wound around the tube.

18. The column assembly of claim 16, wherein the heating element wraps around the tube, and the capillary column wraps around a combination of the heating element and the tribe.

19. The column assembly of claim 16, wherein the capillary column wraps around the tube, and the heating element wraps around a combination of the capillary column and the tube.

20. The column assembly of claim 16, wherein a portion of the tube forms a loop, wherein the heating element comprises an elongate wire helically wound around said portion of the tube, and at least a portion of the capillary column wraps around a combination of the elongate wire and the portion of the tube.

* * * * *